United States Patent [19]

Zetter et al.

[11] Patent Number: 4,732,155
[45] Date of Patent: Mar. 22, 1988

[54] IMPLANTABLE CHEMOATTRACTANT SYSTEM

[75] Inventors: Bruce R. Zetter, Cambridge; Robert S. Langer, Somerville, both of Mass.

[73] Assignee: The Children's Medical Center Corporation, Boston, Mass.

[21] Appl. No.: 769,946

[22] Filed: Aug. 27, 1985

[51] Int. Cl.⁴ .................................................. A61B 5/00
[52] U.S. Cl. ..................................... 128/630; 128/632; 128/637; 128/749; 128/769; 435/284; 435/287; 424/9
[58] Field of Search ................ 435/284; 128/632, 637, 128/630

[56] References Cited

U.S. PATENT DOCUMENTS 3,998,211 12/1976 Bucalo ................................. 128/769
4,164,560 8/1979 Folkman et al. .
4,357,312 11/1982 Hsieh et al. .
4,391,797 7/1983 Folkman et al. .

OTHER PUBLICATIONS

Langer et al–Chem. Abst., vol. 92 (1980) p. 142838c.
Michel et al–Chem. Abst., vol. 103 (1985) p. 121,236k.
Bailey et al–Chem. Abst., vol. 103 (1985) p. 101,655t.
Langer et al., *Canad. J. Microbiol.* 26(2):274–279 (1980).
Bailey et al., *J. Protozool.* 32(2):341–346 (1985).
Michel and Dubertret, *Brit. J. Dermatol.*, 113, Supplement 28:61–66 (1985).
Saxena (1960) Arch. Int. Pharmacodyn. CXXVI:2-28–237.
Ford–Hutchinson et al. (1978) Journal of Pharmalogical Methods 1:3.
Snyderman et al. "Methodology for Monocyte and Macrophage Chemotaxis" in Leukocyte Chemotaxis, Gallin et al. Ed. Raven Press, NY 1978.
Wilkinson (1982) J. Immunolog. Meth. 51:133–148.

*Primary Examiner*—Sam Rosen

[57] ABSTRACT

A system for providing sustained prolonged release of a chemoattractant to a surrounding biological medium which contains cells responsive to the chemoattractant. The system consists of a biocompatible, non-inflammatory body, which sequesters the chemoattractant and allows sustained prolonged release of the chemoattractant from at least one part of the body. A cell trap is positioned adjacent to the releasing portion of the body, so that the released chemoattractant is transmitted through the trap and attracted cells are trapped in it.

16 Claims, 2 Drawing Figures

IMPLANTABLE CHEMOATTRACTANT SYSTEM

BACKGROUND OF THE INVENTION

This invention relates to attraction of cells by chemicals.

Cells may be attracted to a chemical signal called a chemoattractant. For example, white blood cells localize in body tissue where trauma has occurred as a result of attraction by chemicals secreted by the tissue surrounding the trauma.

It may be desirable to investigate the inflammatory response triggered by a substance, for example to evaluate the allergenic effect of ingredients in a cosmetic designed to be administered to the skin repeatedly over long periods. Currently, one way to conduct such tests is to inject the substance subcutaneously into a mammal, e.g. a rabbit, and then to determine the degree of inflammatory response at the injection site. One particular test involves injecting the substance into rabbit eyes.

Apart from injection, a chemoattractant chemical may be evaluated using a device which releases the chemical and collects cells attracted by it. Such devices permit tests to be performed in vivo or in vitro and include inert materials such as pith, agar, collagen or polyurethane sponges into which the chemical of interest is impregnated. After insertion into living tissue or, after an in vitro experiment, the cells which accumulate in the materials can be extracted and examined.

Ford-Hutchison et al. 1978 (Journal of Pharmalogical Methods 1:3) discloses inert porous polyurethane sponges implanted subdermally into rats. These sponges were impregnated with substances such as latex, Zymosan A, Yeast or heat-killed bacteria. Non-impregnated sponges gave mild inflammatory responses, whereas sponges containing one of the above substances attracted specific cell types. These cells were collected in the sponge and their number could be estimated by squeezing liquid from the sponge.

SUMMARY OF THE INVENTION

This invention features a system for providing sustained prolonged release of a chemoattractant to a surrounding biological medium which contains cells responsive to the chemoattractant. By "sustained prolonged release" is meant that a desired level of administration of the chemoattractant is sustained for at least six days. The system consists of a biocompatible, non-inflammatory body which sequesters the chemoattractant and allows sustained prolonged release of the chemoattractant from at least one part of the body. A cell trap is positioned adjacent to the releasing portion of the body, so that the released chemoattractant is transmitted through the trap and attracted cells are trapped in it.

In the preferred embodiment, the sequestering, releasing body is constructed from a matrix of ethylene vinyl acetate copolymer. This matrix is impermeable to cells and large molecules and thus sequesters the chemical to be studied in an environment which protects it against degradation. The releasing body is preferably designed to provide directional release, e.g. by the use of surfaces oriented to promote directional release or by limiting release to a surface area of less than ¼ of the total surface area of the body. For example, a small hole in the matrix permitting release of the chemical is covered with a web of fibers which is also permeable to the chemical. The web has openings larger than the cells, and exhibits a surface electrostatic charge to retain cells entering the web. Cells are trapped within the web fibers, which can be later fixed and sectioned by standard techniques. A synthetic polyester fiber such as Dacron (Reg. TM, E.I. DuPont Co., Wilmington, Del.) is a preferred web material because it has a surface electrostatic charge which facilitates the retention of cells within it.

The invention is particularly useful for evaluating the inflammatory response that a particular substance generates over time, because the invention enables prolonged controlled release of the substance at a particular site. The invention is also useful because it allows a determination of the specific quantity and type of cells attracted by the substance. For example, by sectioning the cell trap and examining the cells in it, the cells attracted by the substance can be categorized as to neutrophiles, monocytes, etc. thus enabling a more precise characterization of the immune response.

The invention is also useful for attracting specific types of cells other than those mentioned above, and for evaluating the ability of a substance to attract other specific types of cells.

Other features and advantages of the invention will be apparent from the following description of the preferred embodiment and from the claims.

DESCRIPTION OF THE PREFERRED EMBODIMENT

The Drawings will first briefly be described.

Drawings

STRUCTURE

Figure 1:
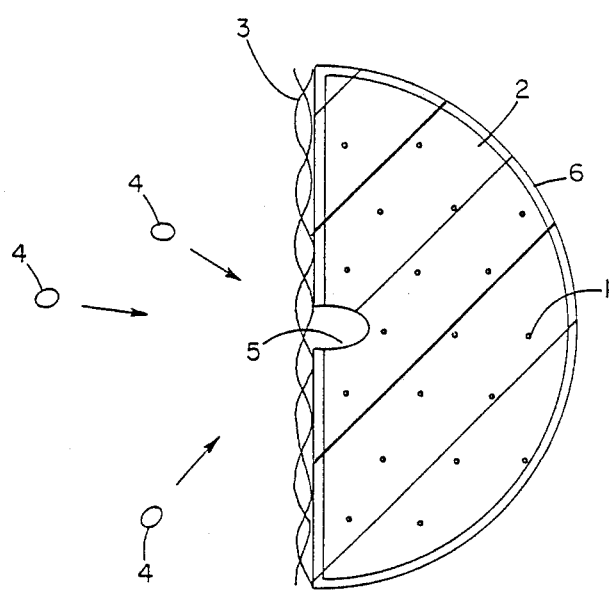
FIG. 1 is a diagramatic representation of the cell attractant system.

Referring to FIG. 1, the polymer matrix 2 containing the chemoattractant 1 is a hemisphere that has a small aperture 5 on its flat face, covered by a polyester material 3. The attractant chemical 1 is released from the polymer matrix 2 through the small aperture 5 and the Dacron material 3, to attract cells 4 towards the apparatus. As described below, the cells 4 are trapped within the polyester material 3 and remain there until the apparatus is removed from its place of implantation.

The polymer matrix is selected to enable slow and steady release over a prolonged period of time (more than six daYs). This matrix sequesters the chemoattractant and prevents degradation of it by enzymes in the surrounding medium. A preferred polymer matrix material is ethylene vinyl acetate copolymer as described in Folkman et al. U.S. Pat. No. 4,164,560, which is hereby incorporated by reference.

The cell trap is a non-inflammatory, wettable web having an adherent surface; the web is adapted to permit cells to enter but not to leave. The trap should also be easily fixed, embedded and sectioned by standard techniques. In the Preferred embodiment a polyester web (stretched polyester fabric Meadox Medicals, Oakland, N.J.) is used as the cell trap, and is circular in shape with a diameter of 0.5 cm. The web fibers have a diameter of about 10-50 microns. The web weave is such that cells can freely enter spaces between the fibers. Further, the web has an electrostatic charge which facilitates the retention of trapped cells.

FABRICATION

Briefly, this polymer matrix is fabricated by the general method described in Folkman et al., which consists of mixing the chemoattractant chemical with a buffering protein (for example, bovine serum albumin) in water and lyophilizing the mixture. Suitable chemoattractants include, by way of example: Glycyl-Histidyl-Lysine, Alanyl-Glycyl-Seryl-Glutamine, f-Methionyl-Leucyl-Phenylalanine, Glycyl-Histidyl-Glycine, and Valinyl-Glycyl-Seryl-Glutamine from Serva Fine Biochemicals, Garden City Park, N.Y.; collagen type I from Collagen Corp., Palo Alto, Calif.; epidermal growth factor from Collaborative Research, Waltham, Mass.; endotoxin standard, prostaglandin E, and histamine from Sigma Biochemicals, St. Louis, Mo.; Tuftsin from Calbiochem, LaJolla, Calif. and heparin from Elkin-Sinn. The system can be used to evaluate an organism's allergenic response to a substance, for example, to an ingredient of a cosmetic, such as an organic fragrance or cream base.

Specifically, 1.1 milligrams of the chemoattractant are mixed with 674 milligrams of the bovine serum albumin. The resulting dry powder is then suspended in 3 ml. of a 15% solution of washed ethylene vinyl acetate in dichloromethane, vortexed at high speed for 30 seconds, poured into a round glass mold of 2.6 cm diameter and set onto a slab of dry ice to freeze. The frozen gel is then placed at −20° C. for two days and dessicated under vacuum for an additional seven days at 20° C. After drying, the polymer is cut into hemispheres or discs of known weight, for example, about 6.7 milligrams.

The hemispheres or discs are coated with an ethelene vinyl acetate copolymer solution by inserting a 30 gauge needle into the flat face of each hemisphere or disc, freezing the discs in liquid nitrogen and then immediately dipping them, for one second, into a 15% ethelene vinyl acetate copolymer solution. This procedure is repeated once more after the discs have been kept for 24 hours at −20° C. As a result, a coating 6 is formed on the exterior surfaces of the hemispheres. The needles are removed, the discs frozen in liquid nitrogen, and an aperture (diameter 0.58 mm) is drilled through the coating of each disc at the removal point of the needle.

The flat surface of the polymer matrix, including the aperture, is covered with the circular polyester patch by wiping the polymer surface with a cotton swab dipped in methylene chloride and pressing the polyester patch against the resulting sticky surface of the polymer. These devices are stored at −80° C. until used.

USE

The polymer release system described above is used to determine the number and type of cells attracted the particular substance that is interspersed in the matrix. Prior to implantation, the polymers are thawed, held within six inches of an ultraviolet source for 30 minutes on each side and incubated in phophate buffered saline, pH 7.4 for 48 hours to allow steady state release kinetics to be obtained. Implantation is performed by standard techniques, e.g. under the skin, with the polyester patch side down. The device can be removed as required, but normally one is removed every day after implantation.

Figure 2:
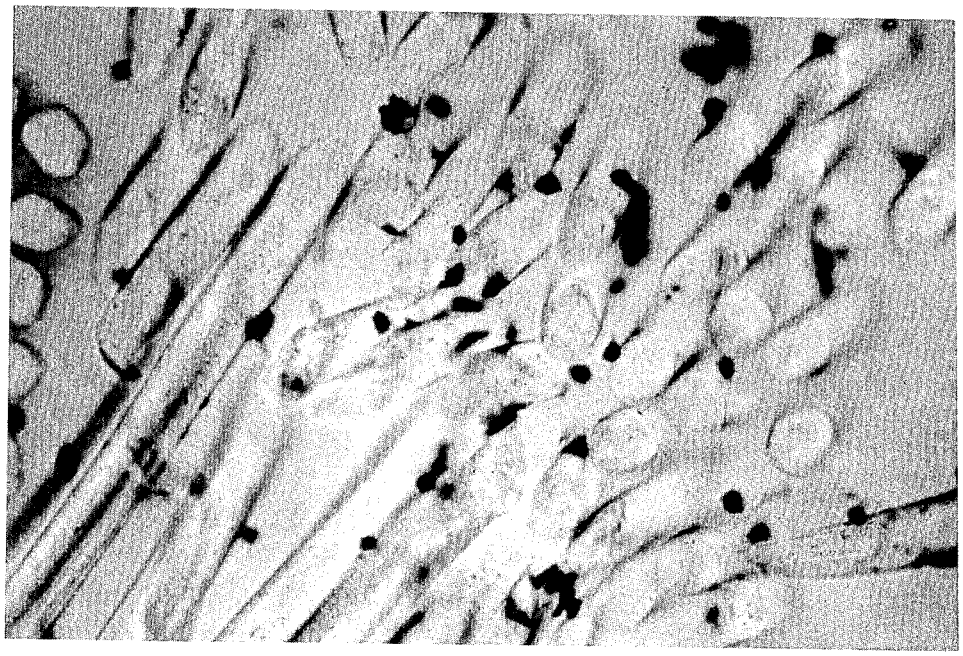
FIG. 2 is a photograph of a cell trap section showing cells adhered to Dacron fibers.

After removal of the implant, the cells attracted by the chemoattractant are counted and evaluated as follows. The device is fixed in 10% glutaraldehyde, the fabric portion embedded in paraplast (Fisher Scientific, Pittsburgh, Pa.) and then cut with a microtome to give sections of four micron thickness. These sections are washed two times for five minutes in parasol solution (Fisher) and then stained using standard histological techniques. For example, Wrights-Giemsa or Safranin O/Fast Green stains are used. These stained sections are then mounted by standard techniques and studied with a microscope to determine the nature and strength of the chemoattractant's activity. FIG. 2 is a photograph of a section of a device that has been prepared as described above showing elongated polyester fibers 3 of 10-15 microns with dark spherical cells 4 adhering to the fibers. The invention enables characterization of cell types. For example, the presence of neutrophiles, but not monocytes or macrophages, is indicative of a relatively mild inflammatory response. The presence of significant numbers of monocytes and macrocytes indicates a more severe response.

OTHER EMBODIMENTS

The method of manufacture of the implantable devices and their shapes or sizes can be easily varied, as can the shape and size of the aperture through which the chemical is to be released. For example, directional release can be obtained from a polymer body having conical or pyrimidal shape. Similarly, other cell traps may be used, for example other non-inflammatory materials formed into webs having holes large enough to permit entrance of the attracted cells.

The device to contain the chemoattractant can be a pump, which may be external to the body, connected by a pipe means to a piece of polyester fabric. Such a pump permits continuous release of chemoattractant for a prolonged period, since it can be readily filled. The sustained release may be at a relatively constant rate, or it may be in spurts that average to a constant rate, e.g. per hour or per day.

We claim:

1. A device for providing sustained, prolonged release of a chemoattractant to cells in a surrounding biological medium and for trapping cells attracted by said chemoattractant, said device comprising:
   (a) a biocompatible non-inflammatory body comprising said chemoattractant sequestered therein, said body providing sustained prolonged release of said chemoattractant from at least a portion thereof, and
   (b) a cell trap comprising a non-inflammatory wettable material attached to said body, chemoattractant released from said body being transmitted through said trap, and cells attracted by said chemoattractant released from said body being trapped by and retained within said trap.

2. The device of claim 1 wherein said body comprises a polymer matrix impermeable to said cells and to said chemoattractant.

3. The device of claim 2 wherein said polymer is an ethylene vinyl acetate copolymer.

4. The device of claim 1 wherein said cell trap comprises a web which allows penetration by cells attracted to said chemical, said web being capable of being fixed and sectioned to examine said cells.

5. The device of claim 1 wherein said cell trap comprises a polymer having openings larger than said cells, said polymer exhibiting a surface attraction for said cells whereby cells entering said openings are retained in said trap.

6. The device of claim 5 wherein said surface attraction is electrostatic.

7. The device of claim 4 or 5 wherein said trap comprises a synthetic polyester fiber.

8. The device of claim 1 wherein said chemoattractant is chosen from:
  (a) histamine
  (b) tuftsin
  (c) Glycyl-Histidyl-Lysine.
  (d) Alanyl-Glycyl-Seryl-Glutamine
  (e) f-Methionyl-Leucyl-Phenylalanine
  (f) Glycyl-Histidyl-Glycine
  (g) Valinyl-Glycyl-Seryl-Glutamine
  (h) collagen Type I
  (i) epidermal growth factor
  (j) endotoxin standard
  (k) prostaglandin E and
  (1) heparin.

9. The device of claim 1 wherein said body is configured to provide directional release.

10. The device of claim 1 wherein only a portion of the surface of said body releases said chemoattractant and said portion comprises less than ¼ of the surface area of said body to provide directional release of said chemoattractant.

11. The device of claim 1 wherein said cells comprise a heterogenous group of cells, and said trap is adapted to be sectioned to determine the cell species in said cell group that are trapped therein.

12. The device of claim 11 wherein said chemoattractant is a substance to be evaluated for allergenic activity.

13. The device of claim 11 wherein said cell group comprises neutrophiles, monocytes, and macrophages.

14. The device of claim 1 wherein said cell trap comprises polyester.

15. A method of measuring the ability of a chemoattractant to attract cells, send method comprising
  providing the device of claim 1 comprising said chemoattractant sequestered in said body;
  contacting said device with a medium comprising said cells; and then
  determining the presence of cells trapped in said trap.

16. The method of claim 15 wherein said contacting step comprises implanting said device within a living animal.

* * * * *